United States Patent [19]

Hinckley

[11] 4,346,216

[45] Aug. 24, 1982

[54] OSMIUM CARBOHYDRATE COMPLEXES

[75] Inventor: Conrad C. Hinckley, Carbondale, Ill.

[73] Assignee: Research Corporation, New York, N.Y.

[21] Appl. No.: 155,163

[22] Filed: Jun. 2, 1980

[51] Int. Cl.³ .......................................... C07H 23/00
[52] U.S. Cl. ........................................ 536/121; 424/4; 424/180; 536/2; 536/20; 536/21; 536/56; 536/102; 536/112; 536/114; 260/429 R; 260/429 J
[58] Field of Search ...................... 536/101, 121, 2, 20, 536/21, 56, 102, 112, 114; 260/429 R, 429 J

[56] References Cited

U.S. PATENT DOCUMENTS

| | | | |
|---|---|---|---|
| 2,609,368 | 9/1952 | Gaver | 536/121 |
| 4,043,952 | 8/1977 | Ganslaw et al. | 536/121 |

*Primary Examiner*—Johnnie R. Brown
*Attorney, Agent, or Firm*—Dennis P. Clarke

[57] ABSTRACT

Osmium carbohydrate complexes prepared by reacting osmium compounds and carbohydrates and their utilization as pharmaceutical compositions for the treatment of heavy metal poisoning and arthritis in mammals. The osmium carbohydrate complexes may also be utilized in X-ray diagnostic procedures as contrast enhancing agents.

6 Claims, No Drawings

OSMIUM CARBOHYDRATE COMPLEXES

BACKGROUND OF THE INVENTION

The present invention relates to certain novel osmium-carbohydrate complexes.

Osmium has been shown to be effective in the treatment of rheumatoid arthritis [I. Boussina, et al, *Scand. J. Rheumatology*, 5,53 (1976)]. Osmium tetroxide ($OsO_4$) has had limited use in the treatment of arthritis. In a typical treatment, $OsO_4$ is injected directly into the affected joints. Following the injection, deposits of osmium containing compounds are found in the injected joint. These osmium deposits may be responsible for the long symptom free periods observed in the treatment. Osmium tetroxide has not found wide utilization, however, due to damaging side reactions which accompany $OsO_4$ injections.

SUMMARY OF THE INVENTION

Novel and valuable osmium compounds are provided by reacting an osmium compound with a suitable carbohydrate.

These osmium-carbohydrate complexes are particularly valuable in the treatment of arthritis by injection at the locus of arthritic disease.

The osmium-carbohydrate complexes may also be utilized to treat heavy metal (e.g. lead) poisoning in mammals due to the ability of the osmium-carbohydrate complexes to chelate heavy metals in mammals.

These osmium-carbohydrate complexes, due to their localization in the kidney and/or liver, may be intravenously administered to mammals as X-ray contrast agents for X-ray diagnostic techniques.

The osmium-carbohydrate complexes may be compounded with conventional pharmaceutical carriers, depending upon the ultimate intended application.

DETAILED DESCRIPTION OF THE INVENTION

Suitable carbohydrates with which osmium may be complexed include Aldoses such as D-glyceraldehyde, D-erythrose, D-threose, D-ribose, D-arabinose, D-exylose, D-lyxose, D-allose, D-altrose, D-glucose, D-mannose, D-gulose, D-idose, D-galactose, D-talose, L-arabinose, L-rhamnose (6-deoxy-L-mannose), L-fucose (6-deoxy-L-galactose), 6-deoxy-D-glucose, D-rhamnose (6-Deoxy-D-mannose), 6-deoxy-D-glucose, L-galactose, D-fucose (6-deoxy-D-galactose), D-glycero-D-galacto-heptose, D-glycero-D-gluco-heptose, D-glycero-D-manno-heptose, and L-glycero-D-manno-heptose; ketoses such as 1,3-dihydroxy-2-propanone (triulose), D-glycero-tetrulose, D-erythro-pentulose (D-ribalose), D-threo-pentulose (D-xyulose, D-psicose, D-fructose, D-sorbose, D-togatose, L-xyulose, and L-sorbose; Heptuloses such as D-allow-heptulose, D-sedopeptulose (D-altro-heptulose), D-altro-3-Heptulose, and D-manno-heptulose; octuloses such as D-glycero-L-galacto-octulose and D-glycero-D-manno-octulose; nonuloses such as D-erythro-L-galacto-nonulose and D-erythro-L-gluco-nonulose; uronic acids such as D-glucuronic acid, D-mannuronic acid; L-guluronic acid, L-iduronic acid, and D-galacturonic acid; aldonic acids such as D-glyceric acid, D-glucoxic acid, and L-gulonic acid; alditols such as erythritol, D-threitol, D-arabinitol, ribital, xylitol, allitol, galactitol, D-glucitol (sorbitol), and D-mannital; disaccharides such as (+)-maltose, (+)-sucrose, (+)-cellobiose, and (+)-lactose; and polysaccharides such as amylose, amylo-pectin, cellulose, glycogen, dextrans, arabinans, arabinoglycans, arabinoxylans, chitin, galactoglucomannans, glucomannans, pectins, xylans, inulins, mannans, agars, agaroses, xanthans, haparins, and hyalurunic acid.

The osmium-carbohydrate complex may be prepared according to several different methods. The direct combination of osmium tetroxide and, for example, glucose and water requires several days for reaction in neutral solution. In a strong base, i.e. 0.01 M KOH, the reaction is complete within 24 hours yielding a black product [elemental analysis 25%Os, 15.4%C, 3.2%H and 14.3%K].

Osmium(VI) complexes react directly with carbohydrates such as glucose to produce brown or black products in a few minutes or hours, depending upon the reaction conditions and reaction proportions. Dipotassium tetramathyl osmate(VI) reacts with glucose in a methanol solution to yield a brown-black product.

Potassium tricetato dioxo osmate(VI) reacts with glucose in glacial acetic acid to yield a brown or black product, depending upon the quantity of carbohydrate available for reaction and the reaction conditions employed. In situations in which there are two equivalents of glucose per equivalent of osmium, the product is black and contains 20 to 50% osmium. Larger quantities of glucose, or excess gluconate, results in a brown product with 10 to 20% osmium. Mild re-fluxing conditions (e.g. steam bath) favors the formation of the brown product.

Osmium analyses to determine the nature of the product formed may be as follows. First, the osmium in the complex is oxidized to osmium tetroxide utilizing one of several effective oxidizing agents, e.g. potassium permanganate or cerium sulfate. Secondly, an acidic thiourea solution is added to the oxidized product forming the intensely rose colored complex $[Os(SC(NH_2)_2)_6]^{+3}$. Osmium concentrations are determined photometrically at 480 mu. By titrating the oxidant in the first step, the ratio of oxidant required to reach end point to the amount of osmium determined photometrically may be computed.

The resulting complexes comprise mixtures of the brown and black products, the precise ratio depending upon the reaction conditions and method of preparation.

The invention will be illustrated by the following non-limiting examples which are directed to the preparation and utilization of osmium-glucose complexes.

Preparation of Osmium-Glucose Complex

Dipotassium tetramethyl osmate is prepared by dissolving about 0.5 g $OsO_4$ in 5 ml $CH_3OH$ and adding thereto 10 ml of 1.0 M KOH in $CH_3OH$. The mixture is allowed to stand approximately thirty minutes until a green precipitate of dipotassium tetramethyl osmate is formed. The mixture is centrifuged and the solvent decanted. The precipitate is dissolved in 100 ml of glacial acetic acid and the product (TAKO) added to a 1,000 ml R.B. flask which contains 0.7 g(4 mmoles) of d-glucose and 100 ml of glacial acetic acid.

The mixture is covered and allowed to stand for several days until the blue osmium acetate color disappears. The mixture is gravity filtered to remove unreacted glucose. The acetic acid solvent is removed by rotary evaporation.

The black product is then dissolved in approximately 30 ml H$_2$O and filtered through a sephadex G-25 column to remove unreacted glucose and remaining acetic acid. Water is removed by rotary evaporation and the product dried over P$_2$O$_5$ under vacuum to yield a black product [elemental analysis 35%Os, 14.6%C, 5.8%H, 4.9%K].

The method when repeated utilizing 12 mmoles of glucose yielded a brown product [elemental analysis 13%Os, 26%C, 4.3%H and 13.2%K].

According to another method, potassium triacetato dioxo osmate(VI), TAKO, (2 mmoles, freshly prepared) is combined with glucose (4 to 12 mmoles) in glacial acetic acid (200 ml) and allowed to react at room temperature. In this case, the glucose is dissolved in 10–20 ml of water before being added to the acetic acid, the reaction with TAKO is complete in a day. Without preliminary addition to water, as in the first preparation discribed above, not all of the glucose dissolves in the acetic acid and the mixture with TAKO is allowed to stand for two to three days.

After filtering, the acetic acid solvent is removed by rotary evaporation. The solid is then redissolved in 10–20 ml of water and passed in two aliquots through a Sephadex G-25 column (solvent:water). The compound passes through the column in a broad band, the leading edge of which elutes at the void volume, and is black or brown in color depending upon the osmium/glucose ratio in the reaction mixture.

The composition of the products produced according to the above-described methods is variable, subject to some control by adjusting the quantity of glucose available for reaction with the osmium reagents. For example, a glucose to TAKO ratio of 2:1 in mmoles yields a black product containing 20–30% osmium. Black products containing up to 50% osmium are also obtained. Larger quantities of glucose (ratio 6:1) yield products which are brown and contain 10–20% osmium. Mild heating favors the formation of the brown products. Carbon percentages in all cases indicate bound carbohydrate.

When utilizing 4 mmoles of glucose, a black product was obtained [elemental analysis 20%Os, 24.5%C, 3.9%H and 10%K]. A brown product was produced using 12 mmoles of glucose [elemental analysis 23$Os, 32.4%C, 5.6%H and 6.9%K].

Differences in color and composition are reflected in differences in other properties. Black products have greater osmium content, higher densities and heavier molecules than brown products. In spite of this, the different preparations are closely related. Though wide variations in composition can be achieved, physical and chemical properties appear to be smoothly and closely related to composition.

Gel filtration reveals that the preparations are mixtures of large molecules. The complexes elute in broad bands beginning at the void volume of a Sepharose 6-B column. This indicates that some of the molecules and mixtures have molecular sizes which exceed those of globular proteins having molecular weights of $10^6$ daltons.

In gel electrophoresis studies, the osmium complexes migrate toward the positive electrode demonstrating anionic character. They migrate at rates comparable to bromphenol blue in broad bands which broaden as the electrophoresis proceeds. This indicates a polydisperse mixture which was confirmed according to different experiments. In the first, an osmium complex is electroporesed in agarose or polyacrylamide gel for 2½ to 3 hours. The band is then sectioned and the sections placed on separate gel columns and the electrophoresis resumed. The fraction in each section migrates at a rate proportional to its position in the initially formed band indicating distinct mobilities.

In a second experiment, electrophoresis through gels of different concentrations are compared. Plots of migration versus gel concentrations indicate relative size. These plots show that the trailing edge of the band is made up of larger molecules than the leading edge. Density, viscosity and sedimentation studies reveal that molecular weights for the larger molecules are from 5,000 to 20,000 daltons with some molecules ranging up to 100,000 daltons.

The precise structure of these osmium-carbohydrate complexes is, at present, unknown. The above experiments and studies, however, give rise to the following picture. The complexes are polydisperse mixtures of osmium-carbohydrate polymers. The number of osmium atoms varies from 15 to 50 per molecule most commonly with some having as many as 100 or more. Within the molecules, osmium atoms are linked together with oxygen or carbohydrate bridges. Osmium is in the plus 4 oxidation state and the polymers are anionic. In solution, the molecules are distorted spheres. The above suggests that the organizational geometry is that of coiled chains of varying lengths. The chains may be branched and/or cross linked, but not linearly extended.

The complexes react with proteins, evidence for which is the formation of precipitates in the presence of protein and protein dependent bands in electrophoresis. The proteins studied include albumen, cytochrome C, myglobin and lysozyme. In the experiments, solutions containing an osmium-carbohydrate complex and the protein were mixed and allowed to stand for some time. The reaction is not immediate and the reaction time is dependent upon the osmium content of the complex. Where the osmium percentage is high (i.e. 25%), precipitates form in 2–3 hours. If the osmium percentage is low (15%) precipitates may not form at all. In every case, however, electrophoresis demonstrates the formation of complexes which appear as distinct and narrow bands, present only when protein is present.

Toxicity Studies

In mice, the osmium complexes have no acute toxicity. Toxicity tests include dose levels (interperitoneal) up to 1.0 gm/kg body weight. The tests were performed with groups of four mice with a like number of non-injected controls.

Xray studies of mice immediately following injections show very dense material present in the peritoneal cavity. Thirty minutes later, similar contrast is found in the bladder; however, not in the abdomen, indicating transfer to the blood circulatory system and out the kidneys. Not all of the injected material appears in the urine. Some mice were sacrificed one day after injection and examined internally. Liver and kidneys were found to be discolored, with the kidneys being the most markedly black.

Gel filtration elution diagrams of collected mouse urine from mice injected with osmium complex were compared with those of the compounds before ingestion (Sephadex 6-B, solvent distilled water). In the urine, only low molecular weight fractions were found. Osmium complex fractions which normally elute at the void volume, and present before ingestion were largely absent in the urine.

In another experiment, three groups of five mice were injected daily with 1.0 g/kg body doses of three different osmium complex preparations for five days. During this period, no indication of acute toxicity were observed. Urine was collected and gel filtration of urine samples showed, as before, that low molecular weight osmium containing components were present. The mice were then sacrificed and then examined internally. In this experiment, each mouse had received 5 gm/kg body weight of osmium comlex over a 5 day period. The liver and kidneys were strikingly discolored with a hue that visually matched the color of the injected osmium complex. In these cases, unlike those of only a single osmium complex injection, the heart, lungs, pancreas, visera, and other tissue were also colored. In addition to demonstrating the very low acute toxicity, the studies show that osmium complexes will bind to tissue surfaces and that there are decided binding preferences.

Arthritis Studies

A series of experiments were carried out to determine the binding characteristics of osmium complexes within arthritis diseased joints. In all cases, unless otherwise specified, the black osmium-glucose described in the first example above is employed.

In the first experiment, hock joints were taken from an arthritic adult male hog. The boar had been suffering from acute athritis for more than a month and died of other causes. When the joints were removed and opened, several extensive osteochondritic lesions were found. A 2% osmium-glucose complex solution was applied to the joint surfaces, both involved and uninvolved areas. Although some binding of osmium complex (observed as a discoloration) was found for every tissue treated, a marked preference for the tissue within the lesions was found. The observed extent of preference was time dependent. That is, if the Osmium complex solution was kept in contact with the joint tissue for an extended period (½ hour) the binding within the osteocondritic lesion was extensive, while discoloration of healty tissue remains slight.

Injection of Osmium-glucose complex into an intact arthritic joint of a living pig yielded a similar result. When the joints were opened, discoloration due to osmium complex binding was observed in tissues of the joint capsule and within osteochondritic lesions to a degree depending upon the concentration of the injected osmium complex, the composition of the complex, the quantity injected, and the extent and nature of the arthritic lesions in the joint.

In a specific example, an arthritic hock joint of a live pig was injected while intact with 5 ml of a 2% osmium-glucose complex solution which was then drawn back into the syringe as a wash. 6 ml of the same solution was then injected into the joint. After 24 hours, the pig was sacrificed and the joint removed for examination. Discloration due to complexed osmium was found in the joint capsule and within the arthritic lesions.

Based upon these results, the next injections employed a higher osmium complex concentration (10%), a smaller volume (1 ml) and an osmium complex preparation containing a relatively high osmium content (36%). Three days after injection, the pig was sacrificed and the joints removed and opened. Osmium complex staining within the joint was dramatic and extensive. Every tissue surface was discolored, but definite preferences were found for the arthritic lesions which were intensely black.

An additional experiment of longer duration yielded a similar result. A relatively young pig (3½ months, 70 pounds) which showed evidence of developing arthritis in the hock joints was injected in the right hock with 0.5 ml of osmium-glucose solution (10% solution, 36% osmium). The left hock was not treated. After 4 weeks the pig was sacrificed and the hock joints removed and opened. Surfaces in the treated hock joint were discolored black to dark grey. A nearby lymph node was also blackened. This inidicates that osmium-complex staining in a joint is long term. Once the material adheres it is not readily removed.

This assessment was supported by a secondary observation in this experiment. The weeks following the injection were a time of rapid growth for the pig. Its weight more than doubled to approximately 150 pounds at the time the experiment was terminated. Growth in the treated hock joint is indicated by a network pattern of lightly stained or unstained material. As the surface of the joint grew, new collagen formed and was not stained by the osmium complex which colored surrounding material. A small arthritic lesion was found in the untreated left hock joint which was otherwise normal. No arthritic lesion was found in the treated joint.

A four year old female St. Bernard dog, suffering for 1 year from arthritis of the right elbow with bimonthly inflammatory episodes and a pronounced limp was treated with the black osmium-glucose complex. The complex (73 mg in 4.3 ml of $H_2O$) was injected into the elbow. Within two weeks of the injection the dog stopped limping. X-rays of the treated joint showed improvement in the joint surfaces. After one year the dog was free from symptoms of arthritis.

The osmium complexes may be incorporated in any suitable injection solution, including water. Inasmuch as the comlexes are not toxic there is virtually no upper limit as to the amount that may be administered. Generally, about 50 mg of the complex disolved in 1–2 ml of $H_2O$ is adequate when injected directly into the synovial space of the affected joint to treat human arthritis.

Heavy Metal Poisoning

Heavy metal poisoning in mammals is usually treated by injections with EDTA to chelate the heavy metal, i.e. lead, mercury, etc. Inasmuch as EDTA and other chelating agents are, themselves, toxic, much effort has been directed toward discovering new treating agents for heavy metal poisoning.

The osmium-complexes of the present invention have a high chelating affinity for heavy metals such as lead and mercury. Lead (II) ions form complexes with osmium-carbohydrate complexes. Precipitates form from osmium complex solutions when $Pb^{+2}$ ions are added in quantities equal to or exceeding a 1:1 mmole ratio to the osmium contained in the polymer. At concentrations less than this, precipitates do not form, but electophoresis and ultracentrafugation indicate that soluble complexes have formed.

Administration of the osmium-glucose complexes to mammals suffering from heavy metal poisoning will result in a chelation of the heavy metal within the osmium-complex in a harmless form which is then excreted from the system without further toxic effects on the mammal treated.

X-ray Contrast Agent

Osmium is a heavy metal and an effective xray absorber. The low toxicity of the osmium-carbohydrate complexes of the present invention allow relatively large doses to be administered. The fact that these complexes migrate to the liver and kidney enable their use as X-ray contrast agents in X-ray diagnostic studies of the liver as well as kidney. The absence of iodine which is present in many X-ray contrast agents conventionally used means that there will be no subsequent interference with thyroid activity tests if desired.

I claim:

1. A complex comprising a polydisperse mixture of osmium-carbohydrate polymers prepared by reacting an osmium compound with a carbohydrate selected from the group consisting of aldoses, ketoses, heptuloses, octuloses, nonuloses, uronic acids, aldonic acids, alditols, disaccharides and polysaccharides.

2. The complex of claim 1 wherein said carbohydrate is glucose.

3. The complex of claim 1 wherein said osmium compound is $OsO_4$.

4. The complex of claim 1 wherein said osmium compound is an osmium (VI) complex.

5. The complex of claim 4 wherein said osmium compound is a di-alkali metal tetramethyl osmate (VI).

6. The complex of claim 4 wherein said osmium compound is an alkali metal triacetato dioxo osmate (VI).

* * * * *